US012758897B2

(12) United States Patent
Mehta

(10) Patent No.: US 12,758,897 B2
(45) Date of Patent: Oct. 13, 2026

(54) AUTOMATED CENTRIFUGATION DEVICE AND METHODS TO CONTINUOUSLY SEPARATE COMPONENTS FROM DIFFERENT MIXTURES

(71) Applicant: Sunil Mehta, Morrisville, NC (US)

(72) Inventor: Sunil Mehta, Morrisville, NC (US)

(73) Assignee: ATHEM LLC, Morrisville, NC (US)

( * ) Notice: Subject to any disclaimer, the term of this patent is extended or adjusted under 35 U.S.C. 154(b) by 388 days.

(21) Appl. No.: 18/041,266

(22) PCT Filed: Aug. 21, 2021

(86) PCT No.: PCT/US2021/047037
§ 371 (c)(1),
(2) Date: Feb. 10, 2023

(87) PCT Pub. No.: WO2022/046572
PCT Pub. Date: Mar. 3, 2022

(65) Prior Publication Data

US 2023/0356111 A1 Nov. 9, 2023

Related U.S. Application Data

(60) Provisional application No. 63/189,194, filed on May 16, 2021, provisional application No. 63/069,014, filed on Aug. 22, 2020.

(51) Int. Cl.
*B01D 17/02* (2006.01)
*B04B 7/08* (2006.01)
*C12M 1/00* (2006.01)

(52) U.S. Cl.
CPC ............ *B01D 17/0217* (2013.01); *B04B 7/08* (2013.01); *C12M 47/02* (2013.01)

(58) Field of Classification Search
None
See application file for complete search history.

(56) References Cited

U.S. PATENT DOCUMENTS 4,413,771 A * 11/1983 Rohde .................. B04B 5/0428 494/20
4,939,087 A 7/1990 Van Wie et al.
(Continued)

FOREIGN PATENT DOCUMENTS

EP 2138570 A1 12/2009
EP 3569317 A1 11/2019
(Continued)

OTHER PUBLICATIONS

"International Preliminary Report on Patentability corresponding to International Application No. PCT/US2021/047037 mailed Mar. 9, 2023".

(Continued)

*Primary Examiner* — Krishnan S Menon
(74) *Attorney, Agent, or Firm* — Myers Bigel, P.A.

(57) ABSTRACT

This invention relates to a continuous flow centrifugation device and method of using the device for separation of solids, particles, liquids, or gases from a mixture containing them. The device contains rotating separation chamber in which incoming material continuously enters the chamber via an inlet and the separated materials continuously flow out via two outlets. Solids or heavier materials exit from an outlet tubing, whose opening is placed in a space that is farthest from the center of rotation and has the highest centrifugal force. The liquid/supernatant outlet is placed in the space that is closer to the center of rotation with the lowest centrifugal force. The reference of placement of inlet to solids outlet is in the same direction as the direction of rotation so that the flow of incoming material, directed from inlet to solids outlet, is in the same direction as the direction (Continued)

Perfusion of rotation. All product contact surfaces can be disposable and diverse separation methods for different applications can be executed in a fully automated or manual manner by a controller that manages different inputs and outputs of system components.

20 Claims, 13 Drawing Sheets

(56) References Cited

U.S. PATENT DOCUMENTS

| | | | |
|---|---|---|---|
| 5,154,716 | A | 10/1992 | Bauman et al. |
| 7,442,178 | B2 * | 10/2008 | Chammas ............. B04B 5/0428 604/19 |
| 9,440,243 | B2 | 9/2016 | Chapman et al. |
| 2008/0171645 | A1 | 7/2008 | Borgstrom et al. |
| 2010/0163493 | A1 | 7/2010 | Hein et al. |
| 2011/0207222 | A1 | 8/2011 | Mehta et al. |
| 2019/0329271 | A1 | 10/2019 | Kato |

FOREIGN PATENT DOCUMENTS

| | | | |
|---|---|---|---|
| EP | 3569317 | B1 | 9/2023 |
| JP | 2017524525 | A | 8/2017 |
| WO | 2016025914 | A1 | 2/2016 |
| WO | 2018131605 | A1 | 7/2018 |
| WO | 2019236895 | A1 | 12/2019 |

OTHER PUBLICATIONS

"International Search Report and Written Opinion corresponding to International Application No. PCT/US2021/047037 mailed Dec. 21, 2021".
Extended European Search Report corresponding to EP 21862443. 5; dated Oct. 7, 2024 (7 pages).
Japanese Office Action (including English machine translation) issued in corresponding application JP 2023-535970 on Sep. 25, 2025, (12 pp).
First Korean Office Action issued in corresponding KR 10-2023-7009302 on May 19, 2026 (8 pages, including English translation).
Australian Examination Report No. 1 issued in AU 2021335131 on May 5, 2026 (4 pages).

* cited by examiner

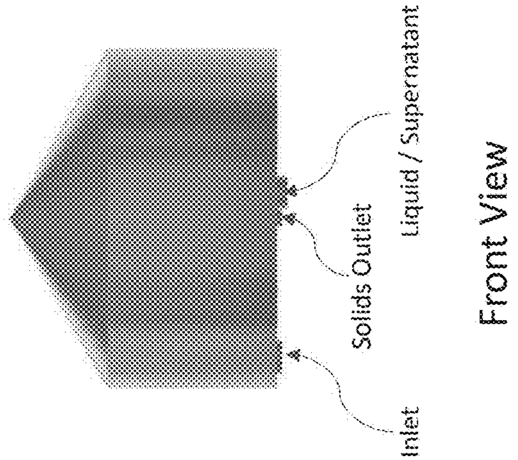
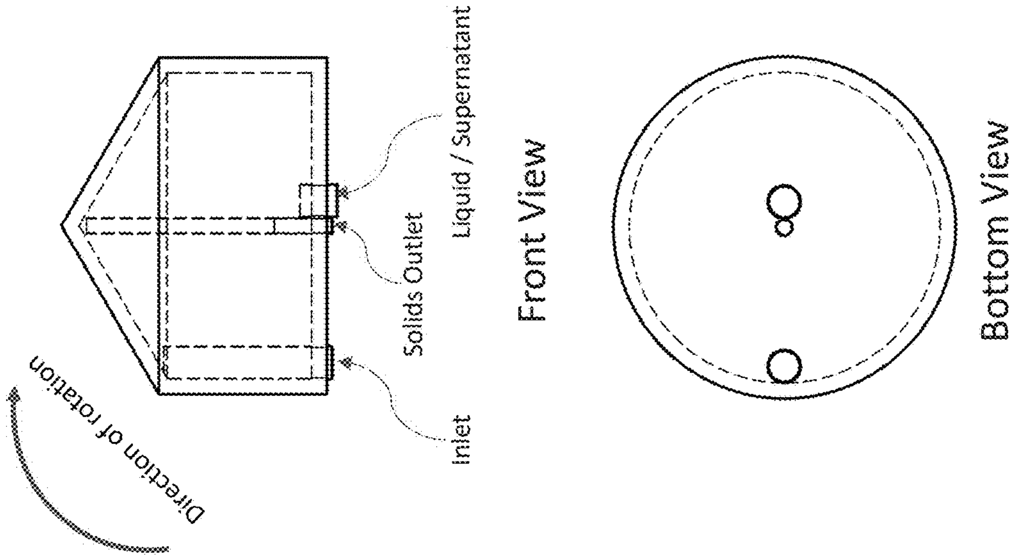
Fig. 3

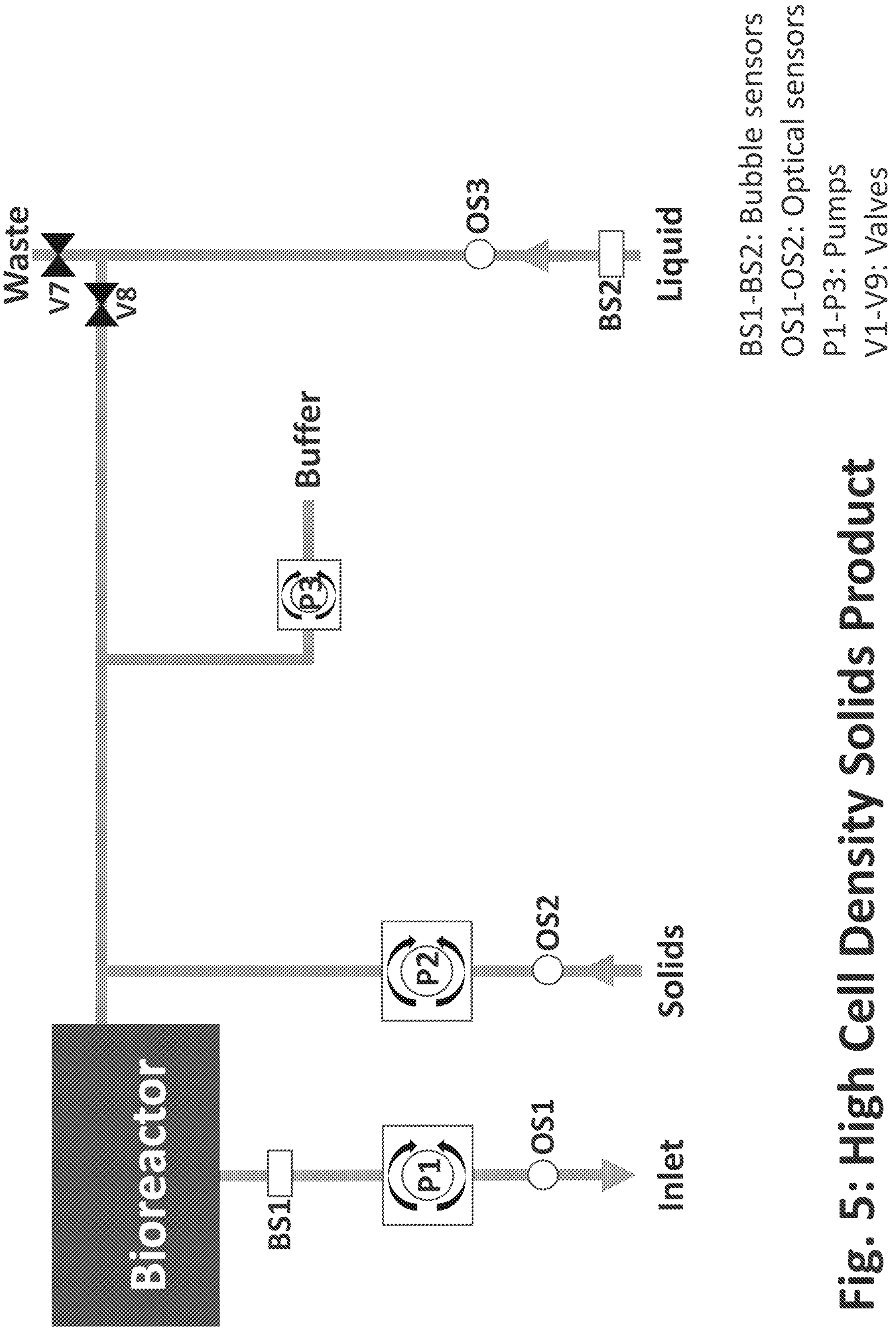
Fig. 5: High Cell Density Solids Product

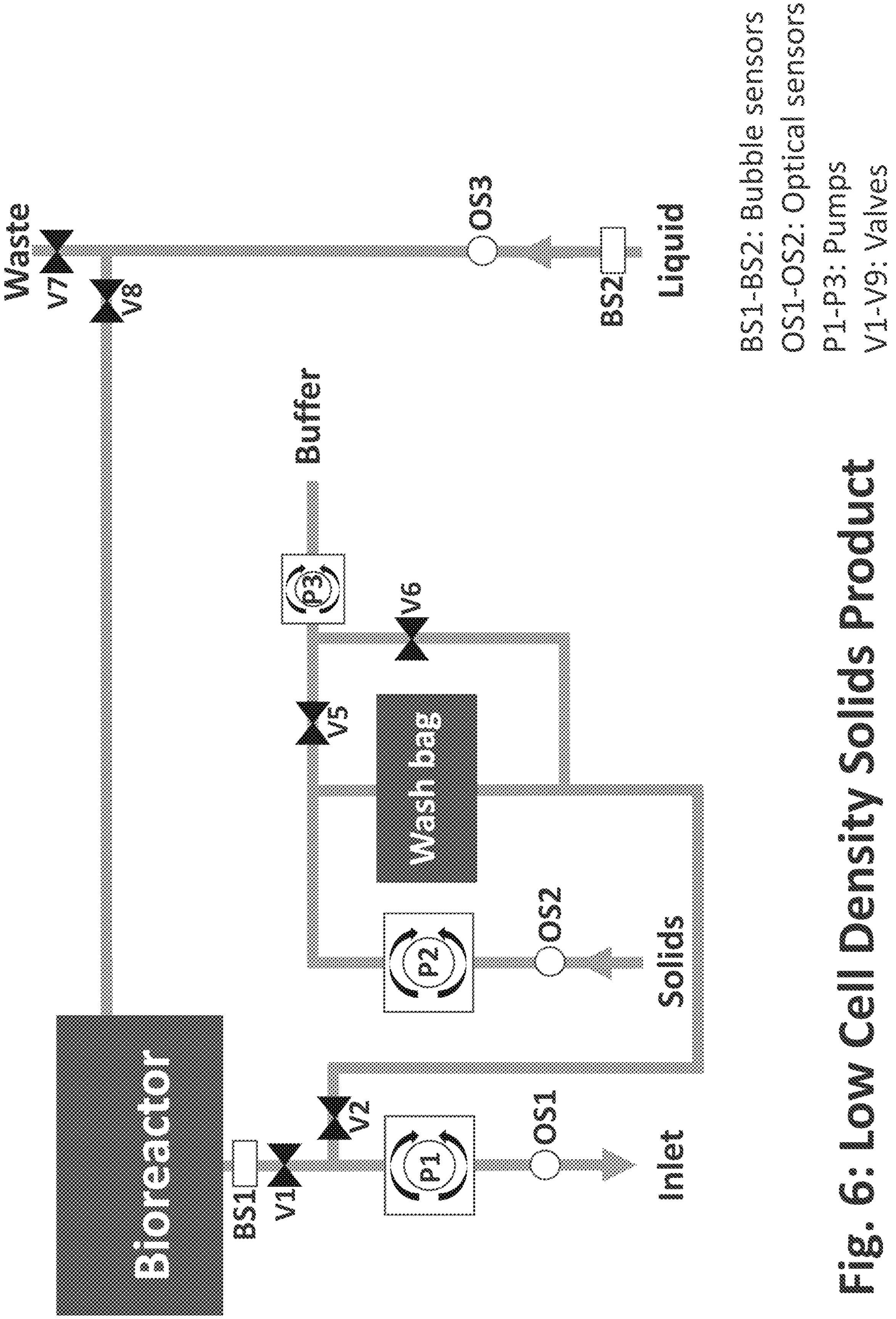
Fig. 6: Low Cell Density Solids Product

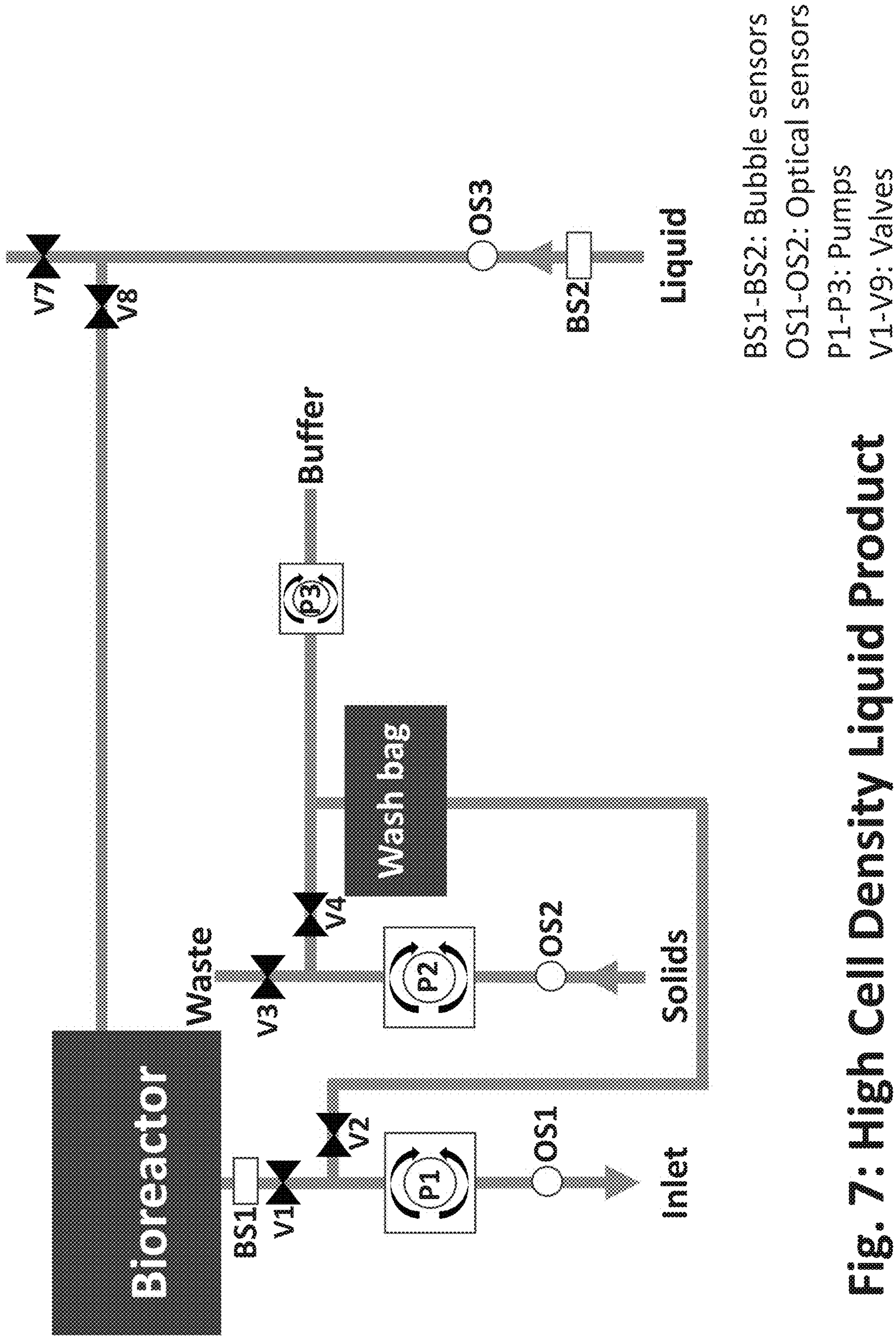
Fig. 7: High Cell Density Liquid Product

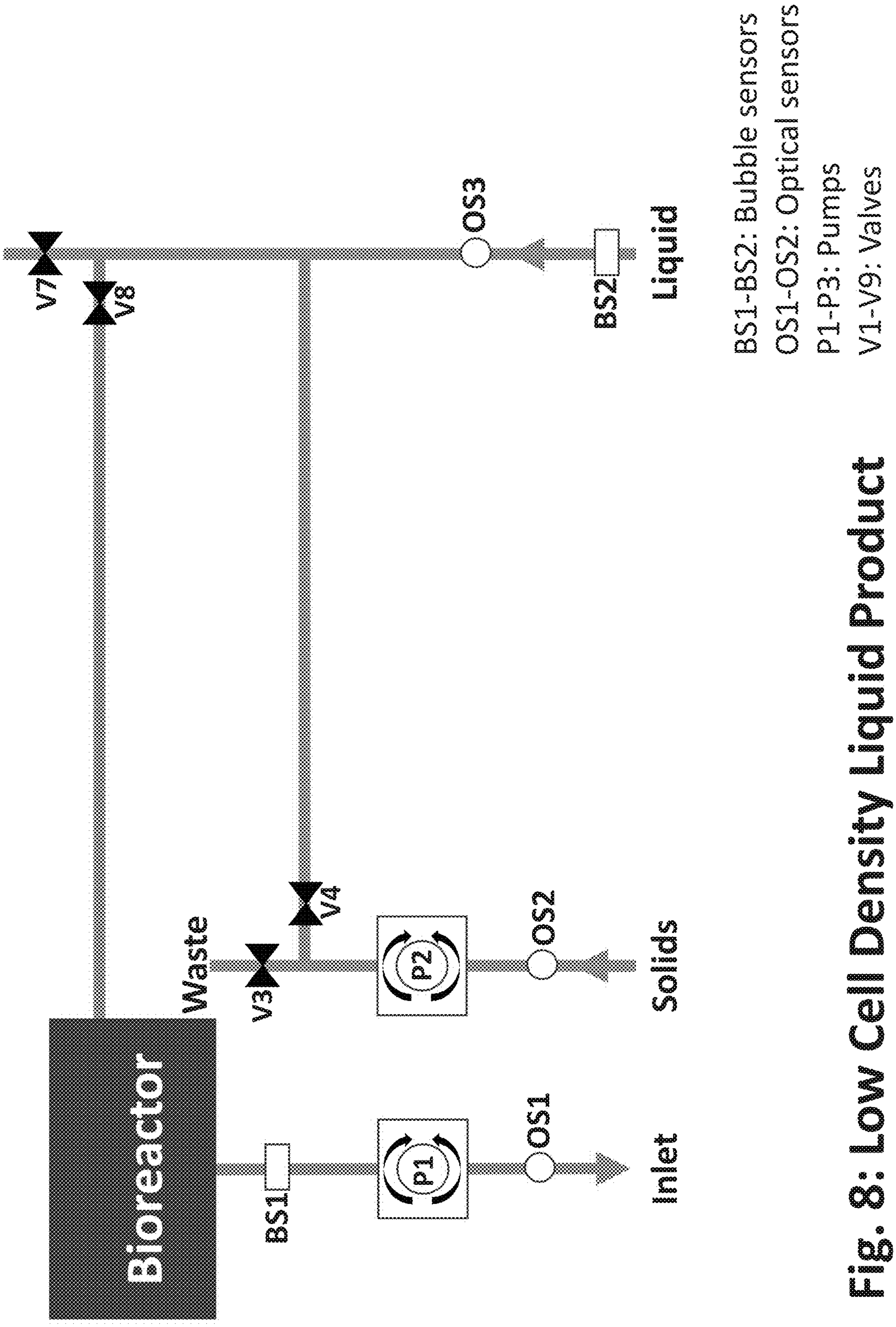
Fig. 8: Low Cell Density Liquid Product

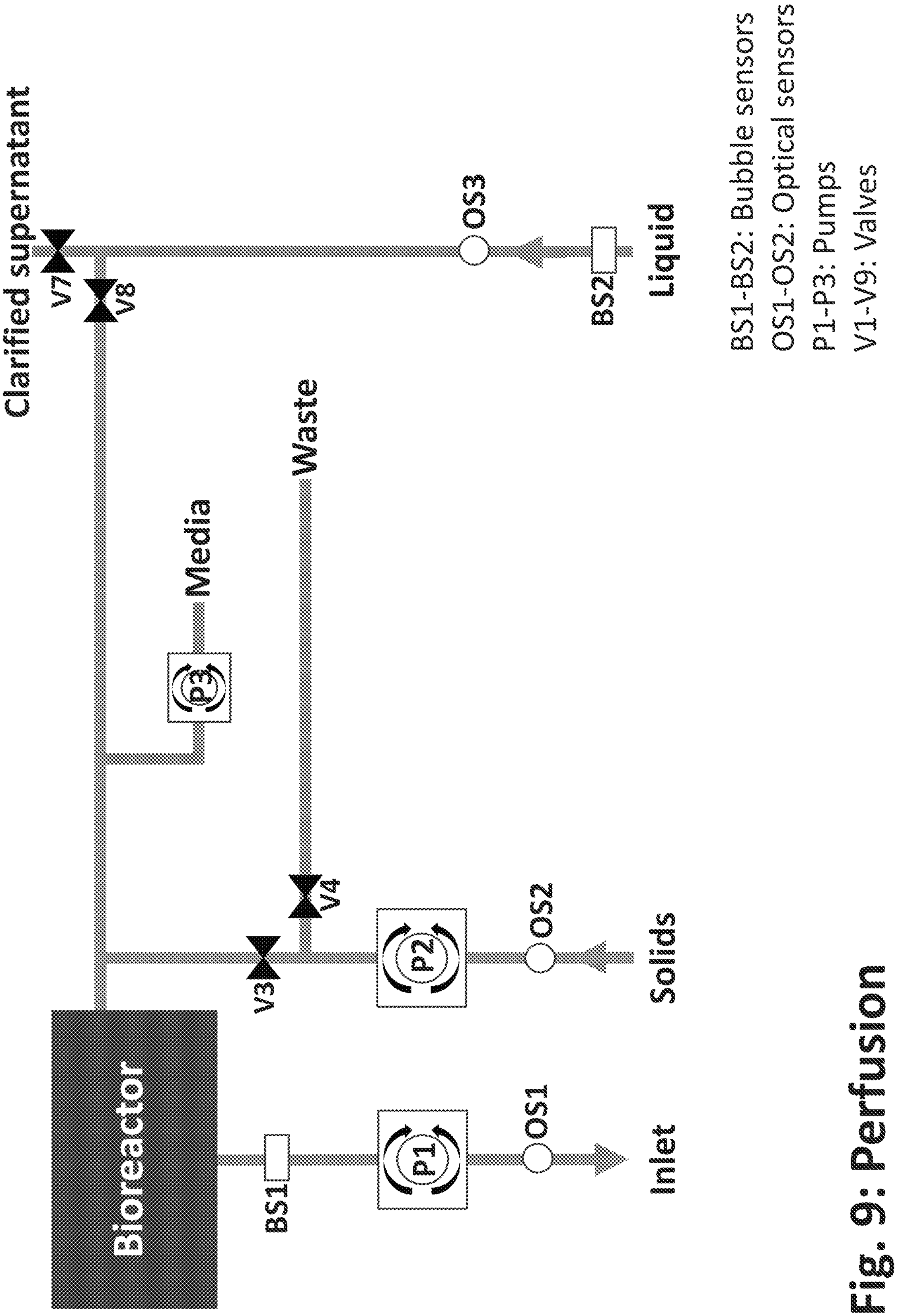
Fig. 9: Perfusion

AUTOMATED CENTRIFUGATION DEVICE AND METHODS TO CONTINUOUSLY SEPARATE COMPONENTS FROM DIFFERENT MIXTURES

RELATED APPLICATIONS

The present application is a 35 U.S.C. § 371 national phase application of PCT Application PCT/US2021/047037 filed Aug. 21, 2021, which claims priority from U.S. Provisional Patent Application No. 63/069,014, filed on Aug. 22, 2020, and from U.S. Provisional Patent Application No. 63/189,194, filed May 16, 2021, the disclosures of each of which are hereby incorporated herein by reference in their entireties.

FIELD OF THE INVENTION

The present invention is related to methods, and systems that are used for separating solids or liquids from a complex mixture based on differences in sedimentation.

BACKGROUND OF THE INVENTION

Separation of specific materials from contaminating materials is a requirement for many processes. For example, most biotherapeutics or vaccine manufacturing processes include steps to purify specific biomolecules from a mixture. Many large industrial processes ranging from energy, food production, or environmental clean-up use separation technologies. There are several applications including vacuum cleaners and air filtration in which separation is routinely employed. Separation technologies predominantly separate particles, liquids, gases, or macromolecules from mixtures. Both centrifugation and filtration technologies are used to separate solid particles from liquids or gases, but centrifugation technologies can also be used to separate liquids from liquids based on differences in specific gravity and/or viscosity. Chromatography is another approach to purify materials but is generally limited to purification of macromolecules rather than particles or different types of liquids.

Centrifugation and/or filtration process are used in virtually all biomanufacturing processes to isolate supernatant or solids, which may be the product or an intermediate product. For example, antibody manufacturing requires separation of antibody containing supernatant from cells (that secrete the antibody) and cell debris. Cells are the product during cell therapy manufacturing, and they are concentrated and washed prior to freezing. Regardless of the location of the virus or recombinant viral proteins (intracellular, extracellular, or cell associated), almost all cell-based vaccine processes require separation between cells and liquid. Large-scale blood processing applications also require separation of different components from the mixture containing plasma proteins, platelets, red blood cells, and white blood cells. Many microbial processes also require separation technologies after fermentation process.

Filtration and centrifugation technologies can sometimes be used for the same process as competing technologies but many times they are used as complementary technologies. Centrifugation technologies mainly exploit difference in size, density, specific gravity, and shape whereas filtration technologies exploit difference in size and charge. Typically, filters are simpler to operate as they do not have any moving parts while centrifuges have rotating machinery. On the other hand, filters offer slower processing, are prone to clogging, have higher operating costs, and generally require large surface areas and floor space as compared to centrifuges.

Most centrifugation technologies for biomanufacturing are based on tubular bowl or disc-stack. Tubular bowl technology is mostly used for microbial cultures as it can generate high centrifugal force (>10,000 g) and can produce paste of solids with low supernatant content. Once the solids fill the bowl, the spinning bowl needs to be stopped to discharge solids. Disc-stack and countercurrent (e.g. kSep, Elutra, and Rotea) centrifuges do not pack the cells tightly but form slurry and intermittently discharge the solids without requiring them to stop during discharges. Countercurrent centrifugation technologies exert low shear, but other bowl or disc-stack centrifugation technologies exert high shear forces and therefore are not used when intact cells are required as a product or an intermediate product. As cells are the product for cell-based therapies and gene therapies and many processes require intact cells (e.g., perfusion or when active vaccine component is intracellular), these technologies are not suitable for many manufacturing processes.

Single-use technologies have recently gained significant traction over reusable technologies for biomanufacturing as they eliminate the need for CIP/SIP (clean-in-place/sterilization-in-place) and risk of cross-contamination between batches. They also reduce cycle times and capital investment. Single-use centrifuges are not so common due to engineering challenges. Low- to medium-speed single-use centrifuges are now available (e.g. Unifuge, kSep, Elutra, Rotea, and CultureOne). Unifuge, kSep, Rotea, and Elutra are bowl centrifuges where Unifuge forms packed bed of solids that require stopping between discharges. kSep, Rotea, Elutra, and CultureOne technologies intermittently discharge solids. kSep, Rotea, and Elutra are low shear technologies that are based on countercurrent flow, and they concentrate solids in a fluidized bed inside a chamber and discharge solids when the chamber is full. CultureOne technology is based on disc-stack and intermittently ejects solids as a slurry.

SUMMARY OF THE INVENTION

The device and the method described here is an automated centrifugation system that continuously discharges solids as slurry and can be single use. The shape of the separation chamber is designed such that multiple forces (e.g., Coriolis and centrifugal) provide superior separation. The system has significant advantages over the existing technologies as it provides continuous operation, superior clarification performance, low shear, and significantly higher throughput in a smaller footprint. The device can be operated in an automatic or manual mode to perform various steps in a process. The system can be operated as a closed system to prevent any contamination. To transport liquid in and out of the system without twisting the tubes, a multichannel tubing can be used that rotates around the rotor at half of the rotor speed. For the applications that require extended run time, a multi-channel rotary union with seals between channels can be used. The individual seals can be o-rings, lip seals, or other type of seals.

BRIEF DESCRIPTION OF THE DRAWINGS

FIG. 3 Detailed description of a chamber with an inlet and two outlets.

FIG. 5 Schematic of a high cell density culture process with solids as product.

FIG. 6 Schematic of a low cell density culture process with solids as product.

FIG. 7 Schematic of a high cell density culture process with liquid or supernatant as product.

FIG. 8 Schematic of a low cell density culture process with liquid or supernatant as product.

FIG. 9 Schematic of a perfusion culture process.

Table 1. Summary of clarification results using small chamber.

Table 2. Summary of clarification results using a scaled-up chamber.

DETAILED DESCRIPTION OF THE INVENTION

Figure 1:
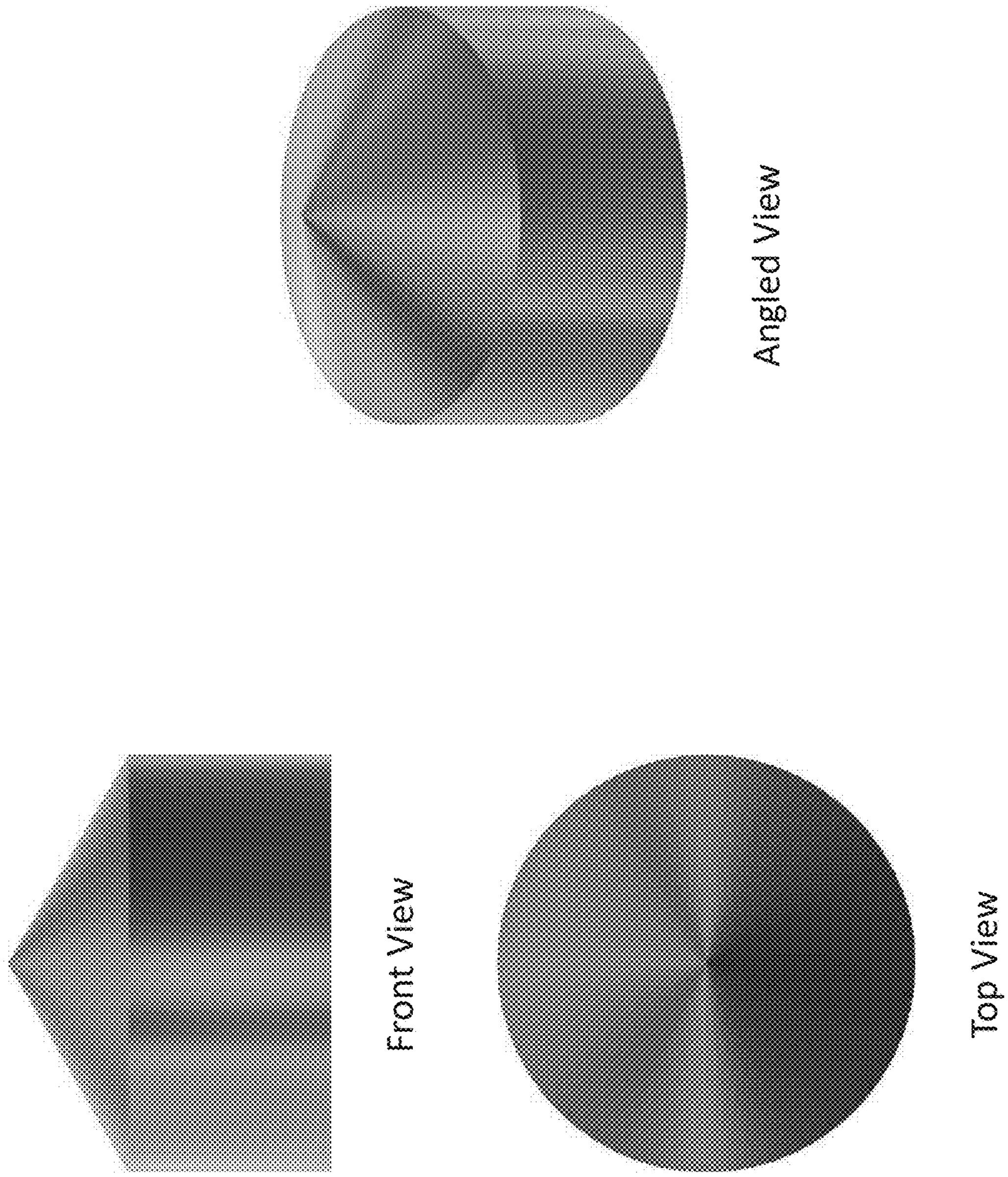
FIG. 1 Conical shaped chamber.
Figure 2:
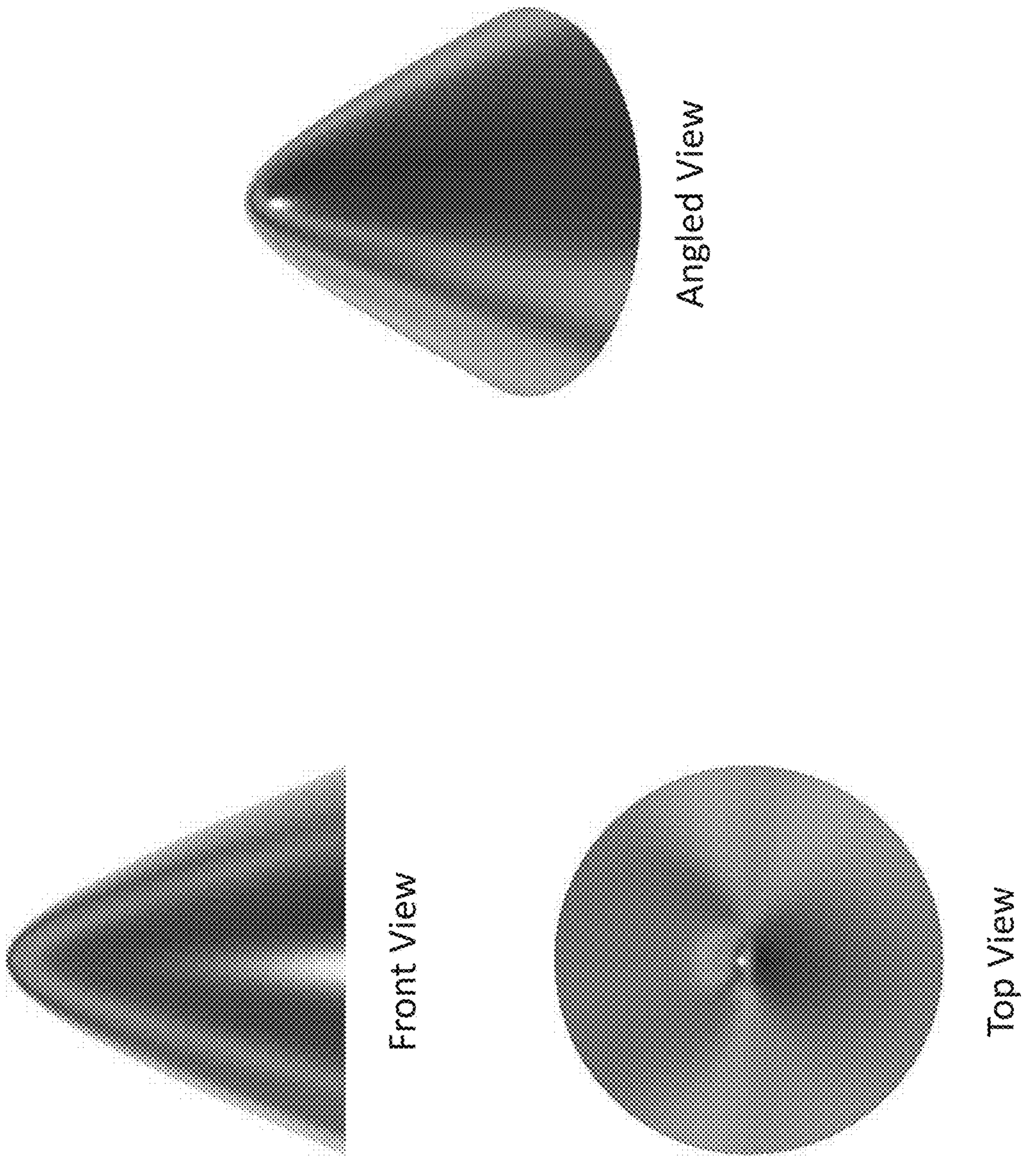
FIG. 2 Paraboloid shaped chamber.

The centrifuge consists of a flexible or rigid insert that is either installed in a rigid rotor or rotates on its own without any external structural support. The rotation can be along the horizontal axis or vertical axis or any axis in between the two. The insert has a shape such that its cross-sectional area stays the same (starting from the center of rotation) and then narrows down (to form apex) along the axis that is perpendicular to the axis of rotation and the apex (or the tip) is farthest from the center of rotation so that the solids can concentrate in the space that has the highest g force. One such shape is a cylinder (near the axis of rotation) followed by cone or paraboloid near the tip. A shape with cone is shown in FIG. 1. The shape can also be such that the area narrows down continuously along the axis that is perpendicular to the axis of rotation. One such shape is a cone or paraboloid (paraboloid shown in FIG. 2). Starting material may contain solids (particles) and liquid, two or more different liquids (heavy and light), or air mixed with particles or liquids. There is one inlet (for the starting material) and two outlets (FIG. 3). Separated solids in the slurry form (from liquids), particles (from liquids or air), or heavy liquids (from lighter liquids) exit the centrifuge from first outlet and clarified liquid or air (from particles or solid) or lighter liquids (from heavy liquids) exit the centrifuge from second outlet (FIG. 3). The outlet from which solids/particles (for liquid-solid or air particles separation) or higher density liquids (for liquid-liquid separation) are collected, is situated in the space that is farthest away from the center of rotation (e.g. placed close to the tip or apex of a cone (FIG. 3) or an paraboloid). Although several different materials can be separated using this device, we will use the example of separation of solids/particles from liquid for most of the illustrations and descriptions. This is not to be construed as a limitation on the scope of the invention.

The reference of placement of inlet to solids outlet is in the same direction as the direction of rotation. The inlet from which the starting material flows in and the outlet from which the solids slurry flows out are oriented in the direction of rotation so that flow of the heavy material (from inlet to solids outlet) is directed in the direction of rotation (FIG. 3). For example, if the direction of rotation is clockwise, the inlet is placed on the left side of the chamber and the outlet for the solids slurry is placed on the right side of the inlet (FIG. 3). On the other hand, if the direction of rotation is counterclockwise, the inlet is placed on the right side of the chamber and the outlet for the solids slurry is placed on the left side of the inlet. This arrangement and shape of the chamber directs the particles or heavier material to follow the wall of chamber to the apex of chamber and concentrate in that space due to Coriolis and centrifugal forces. The direction of the flow of liquid in such manner can be maintained by different ways. One such way is to place the end of the inlet tube closer to the tip and is oriented on the opposite side of the tip in reference to the direction of rotation (FIG. 3 and Table 2, Option 2). In another embodiment, the exit end of the inlet tube is placed in between the bottom of the chamber and the tip and is oriented on the opposite side of the tip in reference to the direction of rotation (Table 2, Option 1). The exit of the inlet tube can also be close to the bottom of the chamber. The liquid/supernatant outlet is located in a space in the chamber that is closer to the axis of rotation with the lowest centrifugal force (e.g. as shown in FIG. 3). In one embodiment, the end of supernatant outlet tubing is placed in the center of base. In other embodiments, the end of supernatant outlet tubing is placed anywhere on the base. If the axis of rotation is vertical, the end of supernatant outlet tubing can be placed towards the highest point of the chamber (on or near the base) so that air is effectively removed during priming (e.g. Table 2, Option 1). If the axis of rotation is horizontal, the end of supernatant outlet tubing can be placed anywhere on the base as the air will be removed while the rotor is rotating during priming (e.g. FIG. 3).

To maximize throughput and efficiently utilize the footprint of a rotor, multiple inserts can be placed in a rotor or a single insert is made with multiple cones/paraboloids. When multiple individual inserts are placed in a rotor, the main inlet and outlets are split so that each chamber has one inlet, one outlet for solid, and one for liquid. Pumps are used to feed or remove liquids and slurry. The solids outlet from each chamber can be connected to an independent pump or pump head for consistent removal of solids from each chamber. In one embodiment, peristaltic pump is used to pump in the starting material through the inlet line and another pump with multiple pump heads is used to pump out the solids slurry from individual solids outlet lines.

Figure 4:
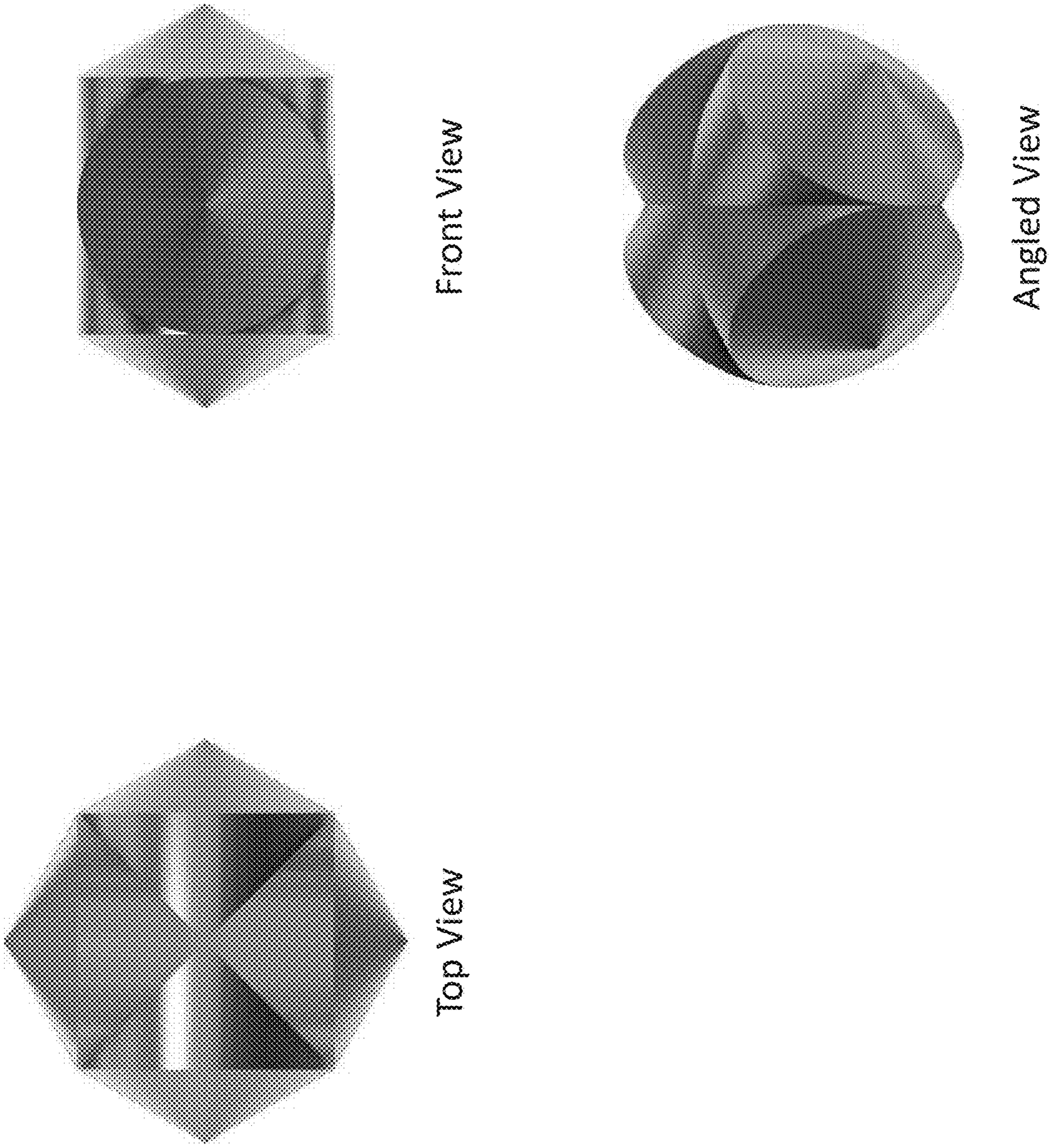
FIG. 4 Example of a single insert with multiple chambers combined.
Figure 10A:
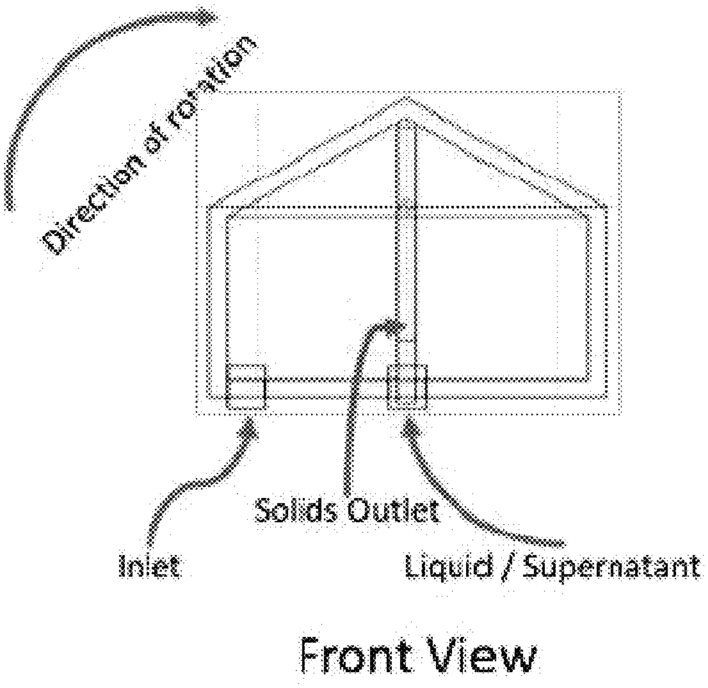
FIG. 10A Schematic front view of a chamber having a short inlet.
Figure 10B:
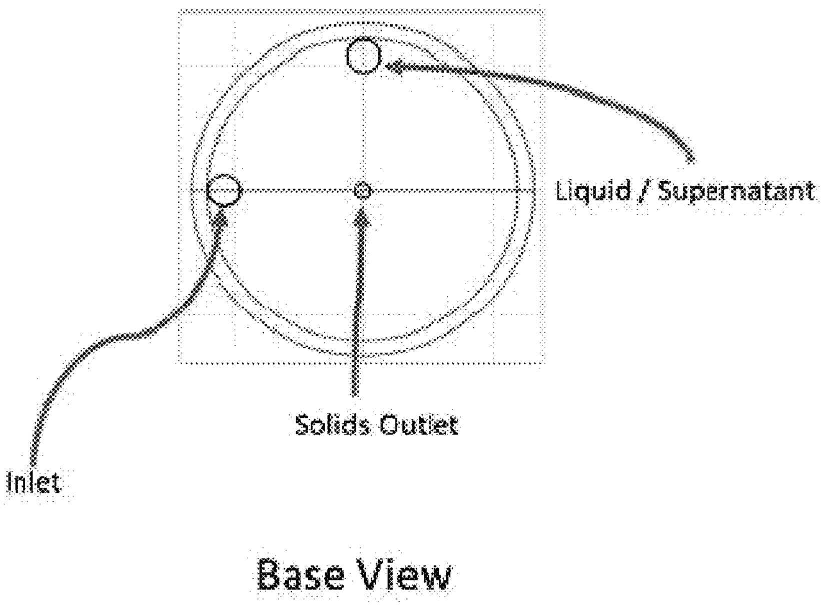
FIG. 10B Schematic base view of the chamber shown in FIG. 10A
Figure 11A:
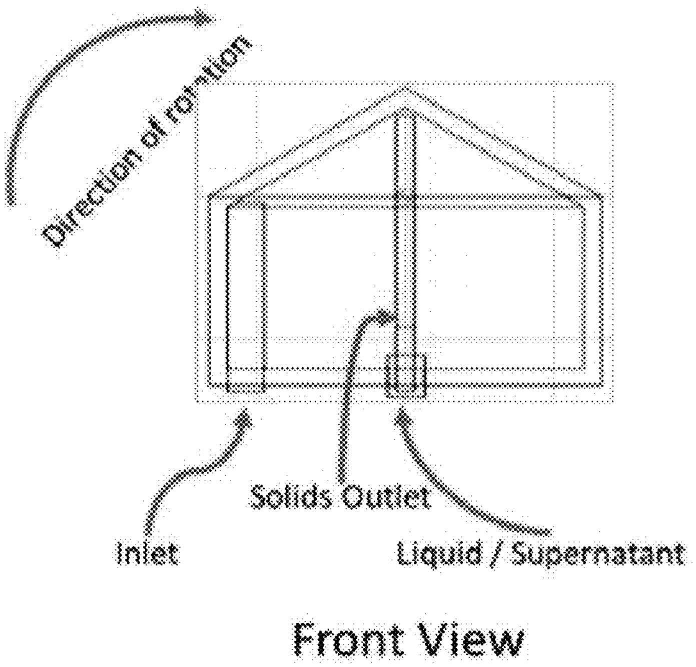
FIG. 11A Schematic front view of a chamber having a long inlet.
Figure 11B:
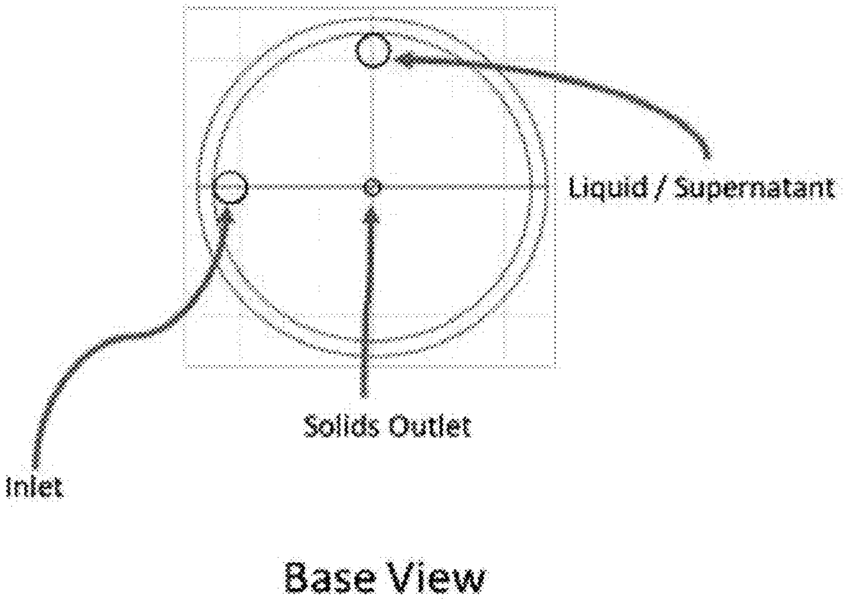
FIG. 11B Schematic base view of the chamber shown in FIG. 11A.
Figure 12:
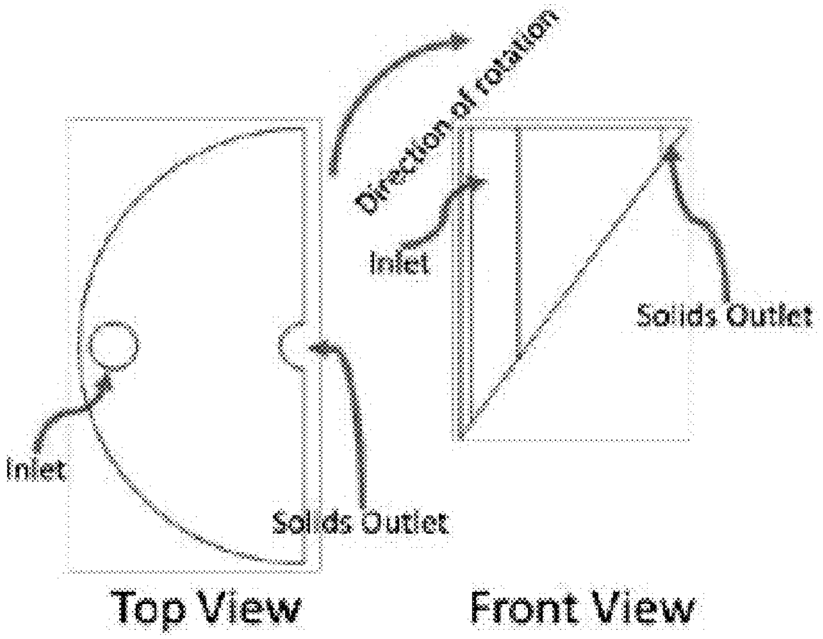
FIG. 12 Schematic top and front views of a chamber having a semi-circular reflector.
Figure 13:
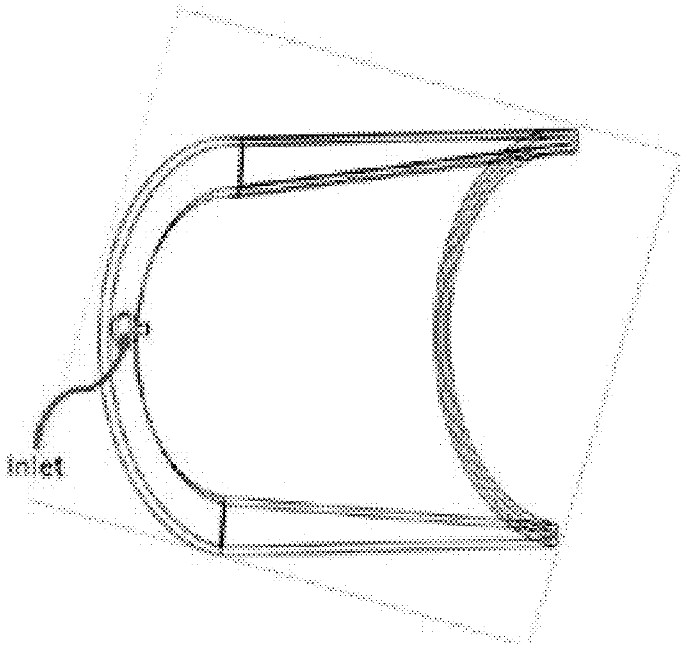
FIG. 13 Schematic of a chamber having an inlet flow distributor.
Figure 14:
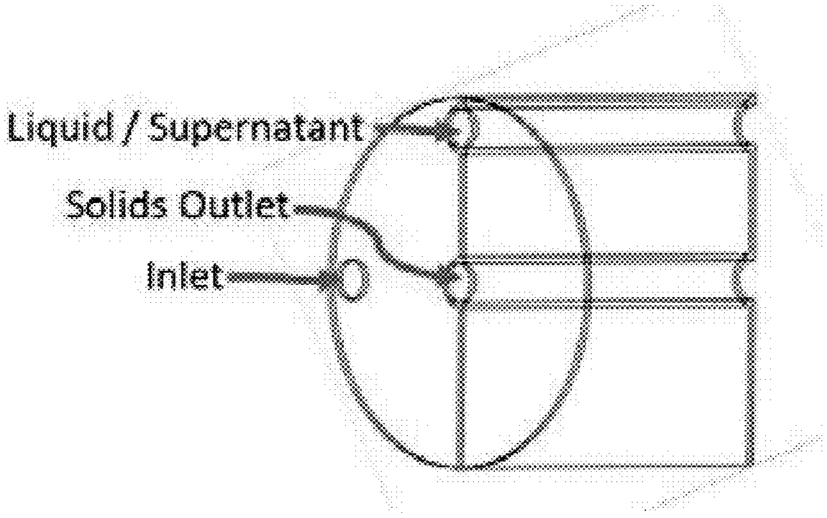
FIG. 14 Schematic of a chamber having a partition with the inlet and the supernatant outlet on opposite sides.
Figure 15:
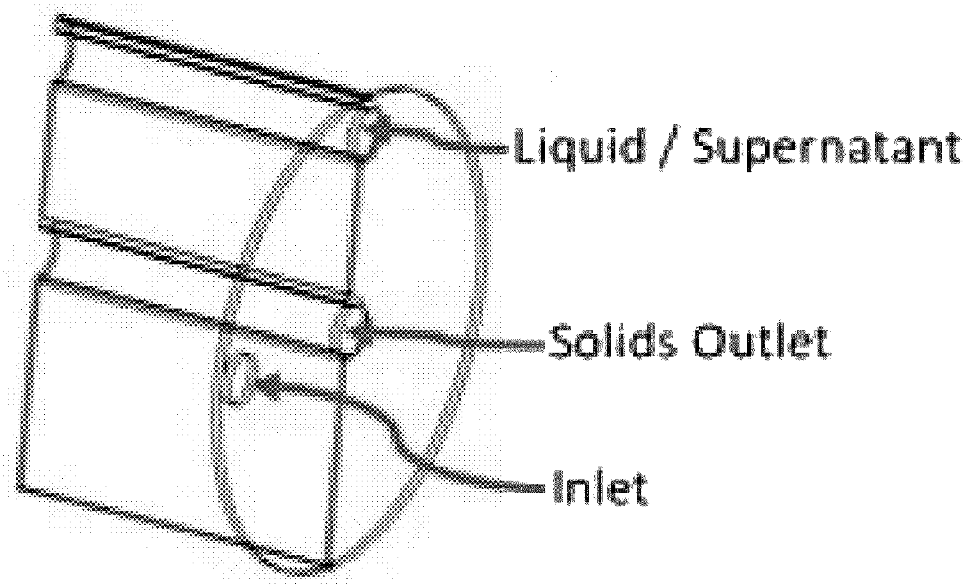
FIG. 15 Schematic of a chamber having a partition with the inlet and the supernatant outlet on the same side.

When multiple chambers are combined to form a single unit or insert, each chamber can have an individual inlet (from a combined incoming inlet tubing) and solids slurry outlet, but combined liquid outlet. In one embodiment, four chambers with cone are combined into a single unit or insert (FIG. 4).

The clarification can be improved by optimizing the liquid flow inside the chamber. In one embodiment, clarification is improved by introducing a partition in the center of the chamber extending from the base to start of the cone shape (Table 2). The partition is perpendicular to the plane of rotation. The supernatant outlet can be on either side of the partition, but results show that clarification is slightly better if the supernatant outlet and the inlet are on the same side of partition (Table 2, Option 1 with partition having supernatant and inlet on the same side). In another embodiment, a half disk shape is used to reflect the downward flow (Table 2). This semi-circular disk is placed where the cylindrical shape transitions to the conical shape and is oriented parallel to the base. The circular part of the disk is oriented on the same side as the inlet and the linear part is oriented towards the solids outlet tube. In this case, solids start to accumulate under the semi-circular disc over time. This accumulation of solids is mitigated by providing a slope from the base of the chamber to the straight edge of the semi-circular part (Table 2, Option 2 with semi-circular reflector). In another embodiment, the flow of the inlet tubing is distributed evenly in the space where the cylindrical shape transitions to the conical shape (Table 2). The distributor can be a structure that transitions from a circular opening (hole) to hollow semi-circular structure at the other end or a larger hollow semi-circle structure that transitions into a tapered thinner hollow semi-circular structure (Table 2, Option 1 with inlet flow distributor).

As the rotor spins, a rotary seal based or umbilical tubing based system (in which bundle of tubes rotate at half speed over the full speed rotor) is used to create fluid paths so that starting material can get in and the separated materials can get out of the rotating system. Rotary seals are commercially available (e.g., from Deublin, Kadant, and DSTI) and umbilical tubing systems have been used in many centrifugation products (e.g., Centritech, Elutra, and kSep). Rotary seals are generally constructed out of metal and are used multiple times. For many bioprocessing applications using this technology, rotary seal is part of the disposable assembly and is used for one batch that may have multiple cycles. In one embodiment, a multi-channel seal is constructed out of plastic (e.g., polycarbonate) with stainless steel bearings on each side. Commercially available multi-channel rotary seals use O-rings as the seals between each fluid channel. These seals are rated for low RPM (~600 RPM) and if they are operated at higher RPMs for prolong duration (>24 hours), they get damaged and start to leak. Several different seal types were developed and tested to improve robustness of rotary seals. In this invention, lip seals are used in between each channel of the rotary seal instead of commercially available O-rings. All product contact surface materials in these seals are suitable for bioprocessing and medical applications. For example, each product contact surface material passes USP Class VI or equivalent testing or is passivated 316L stainless steel. These rotary seals did not fail and exhibited no leakage after operating for 200 hours at 5000 RPM. The rotary seals described in this invention can also be used for other centrifuges or other applications that require movement of liquid with rotation.

Pumps are used to push liquids into the system or pull separated liquids or solids out of the system. For example, peristaltic pumps (e.g. from Cole Parmer or Watson Marlow) are used to pump in the starting material and pump out the solids slurry or clarified liquid from the system at controlled flow rates. The clarified liquid or solids slurry can flow out without any pumping action due to pressure resulting from difference in flow rates between the inlet and outlet (the one connected to pump).

Experiments were performed to determine optimal length, diameter, and apex angle of a single separation chamber. A single polypropylene chamber with PVC or C-Flex tubes (similar to the one in FIG. 3) was rotated along the vertical, horizontal, or intermediate axis at 250 g and 500 g. Slurry with dry *Saccharomyces cerevisiae* and water or 10 micron polystyrene beads (specific gravity of 1.06 g/cm3) in water with 0.01% SDS were used as starting materials for testing. Peristaltic pumps were used to pump materials in and out of the system. The flow rate of starting material (feed flow rate) was started at high flow rate (100 mL/min) and gradually lowered until no beads were detected in the separated supernatant and <5% turbidity was detected in the separated supernatant from yeast cells. Concentrated solids or cells were pulled out of the separation chamber via a peristaltic pump running at a constant flow rate (typically 5-10% of the feed flow rate). Changing the axis of rotation had no effect on the flow rate. The dimensions of the separation chamber and results of experiments are summarized in Table 1. These results show that separation flow rate is directly proportional to the centrifugal force. The increase in length of tube beyond the length equal to its radius did not improve the feed rate. Changes in angle of the apex (70-130 degrees) had small impact on the performance as the feed flow increased by 20% when the apex angle was changed from 70 degrees to 130 degrees. When the orientation of inlet was changed such that inlet to the solids outlet orientation was opposite to the direction of rotation, the separation efficiency was dramatically reduced and required significant reduction in the feed flow rate (>60%) to achieve similar separation.

The flow rate is directly proportional to the cross-sectional area of the tube. To verify this, a polycarbonate chamber with 60 mm internal diameter of the tube was constructed. The results summarized in Table 2 show that ratio of the flow rate of the large chamber to the flow rate of the small chamber remained similar to the ratio of the cross-sectional area of the large chamber to the cross-sectional area of the small chamber. Partition, reflector, or inlet distributor were installed inside the chamber (Table 2) to improve clarification. The results show minimal changes in the flow rate from the original configuration.

The centrifugation system has multiple hardware and disposable components to make the process automated. These include pumps, pinch valves, bubble sensors, temperature sensor, turbidity, or optical sensors. In addition, accelerometer, rotor safety, speed, water leak, and other sensors are incorporated for safe operation of these systems. The complete disposable manifold including insert, tubes, bags, optical sensors, pressure sensors are pre-assembled and sterilized prior to use (via gamma irradiation or Ethylene Oxide). The chambers can be flexible (e.g., constructed with EVA, C-flex, silicone) or rigid (e.g., constructed with polycarbonate, polypropylene, Ultem), The complete assembly is designed to withstanding multiple hours of operation. Tubes or pipes that have single-use product contact surfaces are used to circulate different fluids through the system. For example, flexible silicone, C-flex, PVC, or other tubes can be used to connect different parts of the system to direct fluids. Different open and close configurations of pinch valves create different fluid pathways. Pumps provide the direction of flow for the liquids or slurry of solids. Disposable manifold is connected to bags or vessels containing starting material, different buffers, waste, and separated material via aseptic connectors or welding of thermoplastic tubes.

A controller with HMI (human machine interface) is used by user to automatically or manually control and receive information from parts of the system, which include pumps (speed, direction, start/stop, feedback etc.), valves (open, close, feedback), occlusion/pressure sensors, optical density and turbidity detectors, bubble sensors, pH, conductivity, temperature sensor, weight load cells, accelerometer, speed, and water leak. Some of the sensors (e.g., occlusion/pressure, accelerometer, water leak, micro-switches) are used to improve safety of the system. For example, if one or more of the tubes are occluded, the pressure rise detected by the occlusion detector or pressure sensor will send a signal to the controller and the system will stop he process to avoid high pressure and potential leaks. This information is provided as analog or digital signals to and from the controller. Commercially automation systems from various vendors such as Siemens, Backhoff, or Allen-Bradley are available as complete solutions that include controller, input/output digital or analog cards, and HMI. Examples are Siemens SIMATIC S7-1200 kit, Delta V automation, or Beckhoff TwinCAT 3 automation platform.

User inputs various process parameters into a process screen that is part of the HMI. This can be turned into a recipe that is executed each time a process is run. Process parameters include cycle volume, flow rates, wash, and recirculation times, pH, conductivity, turbidity, optical density and absorbance values to start or stop a step. Once the user starts the process by providing input to the HMI, the controller can automatically run the process using entered process parameters. Multiple valves (FIG. V1-V8) are controlled to form different fluid paths during different phases of the purification process. In one embodiment, pinch valves are used to open and close the fluid path within a flexible tube. A few examples of automated methods to process fluids are described below. The system can run multiple processes using the same hardware, but disposable sets may differ for different processes. The system can be remotely controlled over the internet and can store data or send data to meet CFR part 11 compliance.

Different sizes of chambers (e.g., 1 mm-1 meter diameter) and different centrifugation forces (10-100,000 g) can be used within the device to process a variety of volumes (e.g., 5 mL to 200,000 L). The flow rate of the starting material is directly proportional to the cross-sectional area of the chamber and the g force. For example, if the flow rate of the starting material is 200 mL/min at 500 g, it will be 400 mL/min at 1000 g. Similarly, if the flow rate is 200 mL/min for a chamber with cross-sectional area of 100 square mm, the flow rate will be 400 mL/min for a chamber with cross-sectional area of 200 square mm.

The optimal flow rate for a process can be experimentally determined by pumping the starting material to the device and monitoring the supernatant for breakthrough. The flow rate is adjusted until the amount or the type of solids/cells in the supernatant are at the desired levels. For example, if 5% of the original cell density is found in the supernatant and less than 1% loss is desired, the flow rate will be reduced by 10-20% and the supernatant will be sampled again. This process is repeated until the desired level of loss is achieved. The cell density in the supernatant can be measure by commercially available systems (e.g., Vi-CELL, Cedex, etc.) or by manual counting using a Neubauer hemocytometer. The solids are pumped out of the separation chamber at a higher flow rate than the starting material flow rate multiplied by the percentage of the packed solids content in the starting material. For example, if the packed cell volume in the starting material is 5% and the starting material is being pump in at 200 mL/min, the flow rate for removal of concentrated cells should be greater than 10 mL/min (e.g., 15 mL/min).

In all processes, the disposable manifold is installed, and all connections are made by thermoplastic tube welding or connectors. Priming of the system requires that all inlet lines to the system are filled with liquid before starting a process. There are several ways to prime the system. One possible way is described below (FIG. 5-9).

The system is primed by introducing the starting material into the system via the inlet by running the pump P1 in the forward direction with opened V1 (if used), V6 (if used), and V8 and closed V7. The rotor is spun at a low centrifugal force (e.g. between 2-10 g). Once BS2 or OS3 detects liquid and no air bubbles are detected, the rotational speed is increased to the operating speed (50-20,000 g). The pump P2 runs to remove concentrated solids from the system. Optical sensor OS3 monitors turbidity and when its value becomes stable, V7 opens and V6 and V8 close. This optical sensor OS3 can be used to automatically adjust the flow rates by creating a feedback to improve separation efficiency and can provide alarm if the turbidity increases within the process. For example, in the beginning of a process, the flow rate is gradually increased, and the turbidity is monitored. The highest flow rate that provides lowest turbidity is used for the remainder of the process. If wash buffer bags or any other bags are used, the inlet lines are primed accordingly. This completes the priming step.

There are several applications of this invention. Process for some of the applications is described below. There are many alternate means of performing this process. The examples below are some of the ways these applications are performed. Although a few exemplary embodiments of this invention have been described, those skilled in the art will readily appreciate that many modifications are possible in the exemplary embodiments without materially departing from the teachings and advantages of this invention.

Process to Concentrate and Wash Cells or Solids as Product

Solids, particles, or cells are the desired product in most cell therapy processes, some vaccine processes, and other processes that require solids isolation (e.g., protein precipitation). Many of these processes also require washing or buffer exchange process so that the final product is in a different liquid than it was originally suspended in. Following is the automated process that is used to concentrate, wash, and harvest solids.

The process is setup as show in FIG. 5. Once the priming is complete, V8 is closed and V7 is opened. The pump P1 runs to feed starting material from bioreactor to the centrifuge inlet. The pump P2 runs to remove solids (cells) from the system and transfer those cells back to the bioreactor. The clarified supernatant is discarded to waste from the liquid outlet with opened V7. As the concentration of cells increases with time in the bioreactor, the pump rate of P2 is increased proportionally to avoid very high solids content in the slurry, which cannot be pumped by the pump. Once the desired concentration of cells is achieved in the bioreactor and no washing is required, the process is complete. If washing of cells or solids is required, wash buffer is introduced into the bioreactor by running P3 at the flow rate of P1 minus the flow rate of P2. The amount of wash time needed to reduce the impurities can be calculated using the basic room purge equation or measured experimentally. Once the desired washing is achieved, the cells remaining in the chamber are removed by turning off P1, running P2 and P3 towards bioreactor, closing V7, and opening V8. Once OS3 and OS2 show similar values, P2 is stopped and P1 is run in the direction towards the bioreactor (until turbidity values drop as per OS1) to recover cells in the tube to the bioreactor. After this step, V7 is opened, V8 is closed, and P1 is stopped to recover cells in the tube between P3 and the bioreactor. Thereafter, all pumps are stopped, and the speed of the centrifuge is reduced to low centrifugal force (e.g. between 2-10 g). The process connections to bioreactor, buffer, and connection between centrifuge and liquid tube are sealed by tube sealing or other means. The disposable assembly is removed from all valves and emptied by exposing the Inlet line to air and running P2 towards waste until air is detected by the OS2. The complete disposable manifold can be discarded at this this time.

If the cell density or the solids concentration of starting material is low or high concentration of solids or cells are required at the end of process, an external bag for washing is used since large surface of the bioreactor bag is difficult to rinse and results in higher product losses when final product is transferred to a separate bag. This approach reduces shear on cells as the cells are not recirculated but move in a single-pass from the bioreactor to the external bag. In addition, as compared to the first approach, the pump speed of P2 does not need to be adjusted as the cells are concentrated. In this case, the disposable tubing manifold with wash bag is used as shown in FIG. 6. Once the priming is complete, V7 is opened, V8 is closed, pump P1 is turned on to feed the starting material from bioreactor to the centrifuge inlet with opened V1 and closed V2. The pump P2 runs to remove solids (cells) from the system and transfer those cells to the wash bag. The clarified supernatant is discarded to waste from the liquid outlet with opened V7 and closed V8. Once the bioreactor is empty, BS1 detects air. Washing is initiated by closing V1, opening V2 and V5, and running P3 towards the direction of wash bag. If the volume of cells in the wash bag needs to be reduced to obtain higher concentration of cells, the flow rate of P3 is adjusted much lower than P1. Otherwise, P1 operates at the flow rate that is equal to the flow rate of P2 plus the flow rate of P3. This keeps the volume in the wash bag constant during the washing process. The amount of wash time needed to reduce the impurities can be calculated using the basic room purge equation or measured experimentally. The flow rate of P2 is increased by the concentration factor. For example, if the cells in the original bioreactor volume of 1000 L are concentrated to 100 L, the flow rate of P2 needs to be increased by a factor of 10. Once the washing is complete, the concentrated cells remaining in lines are removed by closing V5 and opening V6. Shortly after the OS2 sensor shows its value closer to that of the buffer (i.e. no or minimal cells are detected), cells in all lines have mostly returned to the wash bag. All pumps and the pinch valves are closed, and the speed of the centrifuge is reduced to low centrifugal force (e.g. between 2-10 g). Some remaining cells in the line between wash bag and V6 are recovered by opening V6 and momentarily running P3 towards the wash bag. After this, the process connections to bioreactor, buffer, wash bag, and connection between centrifuge and liquid tube are sealed by tube sealing or other means. The disposable assembly is removed from all valves and emptied by exposing the Inlet line to air, connecting the line between P2 and V5 to waste, and running P2 towards waste until air is detected by the OS2. The complete disposable manifold can be discarded at this this time.

Process with Liquid or Supernatant as Product

All monoclonal antibodies and many other recombinant proteins are secreted into the supernatant by the cells (mammalian and yeast) that express them. This requires separation of supernatant from the cells. Many upstream processes are being developed to increase the production of recombinant proteins by increasing cell densities.

If the cell densities or solid concentrations are high, product in the supernatant is lost when slurry of solids or cells with some supernatant are discarded to the waste. To maximize recovery of the product lost in slurry, this method washes the concentrated cells before discarding them to the waste. The schematic of disposable assembly is shown in FIG. 7.

Once the priming is complete, V7 is opened and V8 is closed. The pump P1 runs to feed the starting material from bioreactor to the centrifuge inlet with opened V1 and closed V2. The pump P2 runs to remove solids (cells) from the system and transfer those cells to the wash bag with opened V4 and closed V3. At the same time, the pump P3 runs to move the buffer into the wash bag at a defined flow rate. The flow rate of P3 can be calculated using the basic room purge equation or measured experimentally to provide sufficient washing to recover desired amount of product. If higher product recoveries are required, the flow rate of P3 will be higher so that slurry can be more diluted. Once preset amount of starting material has been processed, V2 opens and V1 closes. If very high recovery of supernatant is desired, then the buffer pump P3 continues to run and V4 remains open with V3 closed for a set amount of time. To save time and compromise recovery or when desired washing is achieved, P3 is stopped and after the amount of liquid in the solids line has been replaced with slurry with wash buffer, V3 opens and V4 closes so that washed cells or solids are discarded as waste. Once the wash bag has about 5% of the original volume left, V1 and V4 are opened and V2 and V3 are closed and the P3 runs again to move the buffer into the wash bag at a defined flow rate. This cycle continues until BS1 senses with air bubbles that the bioreactor is empty. The last wash cycle is completed as stated above and at the end of the wash cycle, P3 is run to add buffer until OS2 shows low value and the OS1 and OS2 values are similar (without cells). P2 is stopped and the purging of supernatant is continued until OS3 shows value close to buffer. After this, all pumps are stopped, and the speed of the centrifuge is reduced to low centrifugal force (e.g. between 2-10 g). The process connections to bioreactor and V8, buffer, wash bag, and connection between centrifuge and liquid tube are sealed by tube sealing or other means. The tubing is removed from P1. The disposable assembly is removed from all valves and emptied by running P2 towards waste until air is detected by the OS2. The complete disposable manifold can be discarded at this this time.

The process can be simplified (FIG. 8) if the wash is omitted. This sacrifices recovery but reduces complexity, saves some time, and the need to have a buffer. The reduction in recovery is minimal (<10%) if the cell density or solids content is low (<10% packed cell volume).

Once the priming is complete, V7 is opened, V8 is closed, and pump P1 starts to move starting material from bioreactor to the centrifuge inlet. The pump P2 runs to remove concentrated solids (cells) and discard those to waste (V3 is open V4 is close). The supernatant is collected with opened V7 and closed V8. This process continues until BS1 senses air indicating that the bioreactor is empty. After OS2 detects low solids content (e.g., low turbidity), the disposable assembly is emptied by reducing the speed of the centrifuge (e.g., between 2-10 g), opening V4, and closing V3. The process is complete when air is detected by the OS2. All process connections are disconnected by tube welding or other means and the complete disposable manifold can be discarded at this this time.

Perfusion

Perfusion process is used in the manufacturing of biotherapeutic and vaccine products. This process can be used for products that are secreted from cells or cell-based products. In this process, cell culture is continuously removed from the bioreactor and separated into cells and supernatant. The cells are directed back to the bioreactor and the supernatant is either discarded (if cells are product or intermediate product) or collected (if supernatant contain the desired material). Constant volume of the cell culture in bioreactor is maintained by feeding fresh media into the bioreactor at the same rate as the cell culture is removed. This process is used to continuously generate product in a smaller footprint by achieving high cell densities (20-300 million cells/mL) or to manufacture products that have short half-life or are labile to process-generated impurities. It is a continuous process that can run for prolonged periods (>30 days). The media exchange can be continuous or semi-continuous in the perfusion process. Most perfusion processes require daily bleeding of cells to avoid over accumulation of cells that cannot be supported by the amount of fresh medium that is exchanged. When the culture is discarded every day to bleed the cells, a significant amount (5-20%) of the product is also lost.

Many cell retention technologies have been used to perform perfusion. Alternating Tangential Flow (ATF) is hollow-fiber-membrane based technology in which cell culture moves tangentially across the filter (attached in a housing to the bioreactor) in alternating direction to avoid clogging of the filter. The filtered media containing product is saved for further purification. If the filter pores are smaller than the size of product macromolecule (e.g., for monoclonal antibodies, below 150 kDa), the product is retained in the bioreactor. Major drawbacks of this technology are fouling of filter due to clogging, retention of dead cells and cell debris in the bioreactor, and loss of product during cell bleed and at the end of process (since the cell culture in the bioreactor at the end of process is discarded). Centrifugation and spin filters have also been used as a cell retention device for perfusion. All filtration-based technologies suffer from clogging as the cell concentration increases during the perfusion process. Traditional centrifugation technologies concentrate and discharge concentrated cells in a discontinuous manner. Processes using these centrifugation-based technologies (e.g., Centritech) are not scalable and suffer from cell death as the cells stay in the centrifuge for prolonged period without any oxygenation or process control. One of the advantages of all centrifugation technologies is their ability to separate dead cells and cell debris from live cells due to the differences in their sedimentation velocities.

In the method described below (using the device), the cells are concentrated and discharged continuously in a gentle manner. The residence time of cells in the device is very short (<45 seconds) as compared to other centrifugation technologies. There was no change in the viability of cells (measured by trypan blue exclusion or impermeable fluorescent DNA dye) or Lactate Dehydrogenase content in the cell culture supernatant (surrogate marker of shear) after processing of the cells. Red blood cells (RBCs) can easily be sheared, and the resultant leak of hemoglobin can easily be detected in the supernatant by measuring absorbance at 390 nm. We passed the RBCs through the device (chamber with 60 mm cross-section) 5 times at 50 and 100 mL/min flow rates and did not see any increase in the absorbance value in the supernatant at 390 nm. Positive control for RBC lysis was generated by exposing RBCs to distilled water. These results show that the device described in this invention can handle the cells gently and does not shear cells.

Results from experiments also exhibit that this device can effectively separate dead cells from the live cells and improve or sustain the vitality of cells in the bioreactor. This is also an advantage for all cell therapy processes as cells are the product. Another advantage of this device is that minimal product (in supernatant) is lost during the cell bleeding step as only highly concentrated cells (200-400 million cells/mL) containing a small amount of residual supernatant (in the slurry) are discarded.

In one of the embodiments of perfusion, the centrifuge system described here is connected to a Bioreactor that contains cell culture and the product is in supernatant. The inlet of centrifuge device is aseptically connected to the bioreactor through a tube, the solid outlet of centrifuge device is connected to the bioreactor and waste bag via a Y connector, and the liquid outlet from centrifuge device is connected to the clarified supernatant collection bag and the bioreactor (FIG. 9). Once the priming step is complete, the pump P1 runs to feed starting material from bioreactor to the centrifuge inlet. The pump P2 runs to remove solids slurry (cells) from the system via V3 and pushes those concentrated cells back to the bioreactor. The clarified supernatant is pushed out from the liquid outlet with opened V7 and closed V8. Fresh media can be pumped into the bioreactor by running pump P3 at the same flow rate as the rate of supernatant removal so that the bioreactor volume stays constant. In one of the embodiments, the process continues for a set time (e.g., 30 days). In another embodiment, the above process is run in cycles at 0.5 hr. to 23.5 hr. interval until a set volume of liquid is harvested.

If perfusion cycles are performed, the lines containing cells are washed after each cycle with media by controlling pumps and valves. After turning off all pumps and closing all pinch valves, V8 and V3 are opened and the combined flow rates of pump P1 and P2 is adjusted such that it is equal to or lower than the flow rate of pump P3. Thereafter, P3, P2, and P1 pumps are run towards the bioreactor until OS2 and OS1 sensors show their value closer to that of the media (i.e., no, or minimal cells are detected, and the lines are clean). The rotation of centrifuge and all the pumps are stopped at this stage.

When the process is completed, V4 is opened and V3 is closed to direct cells to waste. Once BS1 senses with air bubbles that the bioreactor is empty, P2 runs until OS2 shows low reading (low number of cells or no cells). The centrifugation speed is reduced (e.g. between 2-10 g), the connections to the waste, media, and V3 to the bioreactor are sealed, and complete manifold is taken out of the valves. The tubing is taken out of the pump P1 and the pump P2 is run in the direction away from the centrifuge to push all the clarified supernatant remaining in the insert. At the end, the centrifuge is stopped, all lines are sealed, and the complete disposable manifold can be discarded at this this time.

If the perfusion process requires cell bleed, V3 is closed and V4 is opened periodically to allow excess cells to go to waste. If the product is in the supernatant and its recovery is required from slurry of cells during cell bleed, the cell bleed can be diluted with a physiological buffer (e.g. PBS or HBSS) and the introduced into the system via inlet, washed supernatant is collected via liquid outlet, and cells are discarded to waste via solids outlet. If the cells are the product or intermediate product, the cells are recovered.

Some modifications to this process can be made to improve efficiency or meet other needs. In one embodiment, media is efficiently utilized to achieve high cell density by connecting two bioreactors to this system to perform media exchange. The process is started by growing the cells in the first bioreactor. Once the desired cell concentration is achieved, this system separates the cells and the supernatant from the bioreactor and the concentrated cells are transferred to the second bioreactor. Fresh media is pumped into the second bioreactor to maintain the desired volume. After complete transfer of cells from the first bioreactor to the second, the cells are grown further or kept under conditions to produce the desired product. Whenever required, the process of transferring the cells from one bioreactor to the other bioreactor is repeated.

Other Applications

The device described in this invention and the components of the device can be applied for many other applications that require manipulation of the cells. For example, to separate microcarriers from cells, separate blood components, separate protein precipitates, chromatography, cell isolation, transfection, infection of cells, coating of cells or particles, activation of cells, and media/buffer exchange.

Many cell therapy and vaccine manufacturing processes require separation of cells from microcarriers as adherent cells are grown on the microcarriers and detached using enzymes (e.g trypsin, collagenase) or chemicals (e.g. EDTA). This process utilizes the automation steps for the "Process with liquid or supernatant as product" as the cells have much lower sedimentation velocity than the microcarriers. At high flow rates and/or lower g force, the microcarriers are concentrated as solids and cells flow through with the supernatant. If the process requires concentration of cells afterwards then steps for the "Process to concentrate and wash cells or solids as product" are used after the microcarrier separation. The washing can be in the final cryopreservation media or formulation buffer so that the cells can directly be banked (for call banking), aliquoted (for cell therapy), or directly cryopreserved. This complete process separates the cells from microcarriers, concentrates, washes, and harvests cells for the next manufacturing processes.

The process to isolate cells or solids as product can be used to effectively separate blood components due to their different sedimentation velocities. In this method, both supernatant and solids are collected, and supernatant is used in the subsequent step. In the beginning, optimal flow rate is used to isolate the heaviest components of blood (e.g., RBCs) while the remaining components flow out with the liquid. In the next round, the RBC depleted blood is fed into the system and concentrated WBCs are collected while the platelets and plasma flow through. Another round of separation can be continued at slower flow rate to isolate concentrated platelets. The platelet depleted plasma flows through as liquid. The system can also be connected to the patient directly as an apheresis system. Same process can be used to separate mixed population of cells or solids due to differences in their sedimentation velocities.

Cells or particles can be coated using this technology using different coating reagents. In this application different solutions are used to coat and wash particles, while the centrifugation system is used for isolating and washing the particles using automated method described "Process to concentrate and wash cells or solids as product". Buffer or media exchanges can also be used to transfect, infect, transduce, or activate cells.

This system can also be used to perform chromatography using chromatography particles that have affinity for product or impurities. The chromatography particles with higher sedimentation velocity than the cells or impurities, are mixed in with the starting material and are separated by the centrifuge as a concentrate. They are then diluted with buffer outside the system for washing and loaded into the centrifuge to be concentrated. Depending upon the application, the impurities or product are eluted from the chromatography particles by mixing them with an elution (to isolate product) or a regeneration (to remove and discard impurities) buffer. This process can be repeated multiple times to recycle the chromatography beads. The chromatography beads can be regenerated after each cycle or after a set number of cycles with regeneration solution (e.g., NaOH solution) In one embodiment, monoclonal antibodies are purified by mixing in Protein A beads with cell culture or supernatant that contains secreted antibody product. The mixture is separated by the centrifuge and the concentrated Protein A beads are washed with buffer to remove nonspecific impurities. After one or multiple rounds of washing and concentration, the beads are incubated with low pH solution (pH <5.0) in a vessel or through inline mixing to elute the concentrated monoclonal antibody product. The beads are washed, regenerated, and can be used again for the next cycle. This process is repeated until the bioreactor is empty.

Although the inventive device and method have been mostly described for bioprocesses, this description is not to be construed as a limitation on the scope of the invention. It will be apparent to those skilled in the art that various modifications and variations can be made to the structure and methodology of the present invention without departing from the scope or spirit of the invention. Rather, the invention is intended to cover modifications and variations provided they come within the scope of the following claims and their equivalents.

REFERENCES

1. MAbs. 2009 September-October; 1(5): 443-452.
2. Subramanian, G. (2014). Continuous Processing in Pharmaceutical Manufacturing: Wiley-VCH Verlag GmbH & Co. KGaA

TABLE 1

| | | | |
|---|---|---|---|
| Tube Diameter (mm) | 26.6 | | |
| Tube Length (mm) | 13.3 | | |
| Apex angle (degrees) | 75 | | |
| Volume (mL) | 10.6 | | |
| Material | | *S.Cerevisae* | 10 um beads |
| Flow Rate (mL/min) @250 g | | 12.5 | 25 |
| Flow Rate (mL/min) @500 g | | 25 | 50 |
| Tube Diameter (mm) | 26.6 | | |
| Tube Length (mm) | 22.0 | | |
| Apex angle (degrees) | 75 | | |
| Volume (mL) | 15.4 | | |
| Material | | *S.Cerevisae* | 10 um beads |
| Flow Rate (mL/min) @250 g | | 12.5 | 25 |
| Flow Rate (mL/min) @500 g | | 25 | 50 |
| Tube Diameter (mm) | 26.6 | | |
| Tube Length (mm) | 19.0 | | |
| Apex angle (degrees) | 130 | | |
| Volume (mL) | 11.7 | | |
| Material | | *S.Cerevisae* | 10 um beads |
| Flow Rate (mL/min) @250 g | | 15 | 30 |
| Flow Rate (mL/min) @500 g | | 30 | 60 |
| Tube Diameter (mm) | 26.6 | | |
| Tube Length (mm) | 8.0 | | |
| Apex angle (degrees) | 130 | | |
| Volume (mL) | 5.6 | | |
| Material | | *S.Cerevisae* | 10 um beads |
| Flow Rate (mL/min) @250 g | | N.D. | N.D. |
| Flow Rate (mL/min) @500 g | | N.D. | 20 |
| Tube Diameter (mm) | 26.6 | | |
| Tube Length (mm) | 13.3 | | |
| Apex angle (degrees) | 130 | | |
| Volume (mL) | 8.5 | | |
| Material | | *S.Cerevisae* | 10 um beads |
| Flow Rate (mL/min) @250 g | | 15 | 30 |
| Flow Rate (mL/min) @500 g | | 30 | 60 |
| Reversed direction of rotation (counterclockwise) | | | |
| Tube Diameter (mm) | 26.6 | | |
| Tube Length (mm) | 13.3 | | |
| Apex angle (degrees) | 130 | | |

TABLE 1-continued

| | | | |
|---|---|---|---|
| Volume (ml) | 8.5 | | |
| Material | | *S.Cerevisae* | 10 um beads |

out of the chamber through the second outlet via a second valve of the plurality of valves.

2. The device of claim 1, wherein the chamber is a tube followed by a cone or a paraboloid.

TABLE 2

| Option 1 (short inlet) | | | | Option 1 with partition having supernatant and inlet on opposite sides | | | |
|---|---|---|---|---|---|---|---|
| Tube Diameter (mm) | 60.0 | | | Tube Diameter (mm) | 60.0 | | |
| Tube Length (mm) | 43.0 | | | Tube Length (mm) | 43.0 | | |
| Apex angle (degrees) | 90 | | | Apex angle (degrees) | 90 | | |
| Volume (mL) | 149.83 | | | Volume (mL) | 144.23 | | |
| Material | | *S.Cerevisae* | 10 um beads | Material | | *S.Cerevisae* | 10 um beads |
| Flow Rate (mL/min) @ 500 g | | 125 | 250 | Flow Rate (mL/min) @ 500 g | | 120 | 240 |
| **Option 2 (longer inlet)** | | | | **Option 1 with partition having supernatant and inlet on the same side** | | | |
| Tube Diameter (mm) | 60.0 | | | Tube Diameter (mm) | 60.0 | | |
| Tube Length (mm) | 43.0 | | | Tube Length (mm) | 43.0 | | |
| Apex angle (degrees) | 90 | | | Apex angle (degrees) | 90 | | |
| Volume (mL) | 149.83 | | | Volume (mL) | 144.23 | | |
| Material | | *S.Cerevisae* | 10 um beads | Material | | *S.Cerevisae* | 10 um beads |
| Flow Rate (mL/min) @ 500 g | | 120 | 240 | Flow Rate (mL/min) @ 500 g | | 130 | 260 |
| **Option 2 with semi-circular reflector** | | | | **Option 2 with partition having supernatant and inlet on the same side** | | | |
| Tube Diameter (mm) | 60.0 | | | Tube Diameter (mm) | 60.0 | | |
| Tube Length (mm) | 43.0 | | | Tube Length (mm) | 43.0 | | |
| Apex angle (degrees) | 90 | | | Apex angle (degrees) | 90 | | |
| Volume (mL) | 125.08 | | | Volume (mL) | 144.23 | | |
| Material | | *S.Cerevisae* | 10 um beads | Material | | *S.Cerevisae* | 10 um beads |
| Flow Rate (mL/min) @ 500 g | | 125 | 250 | Flow Rate (mL/min) @ 500 g | | 120 | 240 |
| **Option 1 with inlet flow distributor** | | | | | | | |
| Tube Diameter (mm) | 60.0 | | | | | | |
| Tube Length (mm) | 43.0 | | | | | | |
| Apex angle (degrees) | 90 | | | | | | |
| Volume (mL) | 142.23 | | | | | | |
| Material | | *S.Cerevisae* | 10 um beads | | | | |
| Flow Rate (mL/min) @ 500 g | | 130 | 260 | | | | |

The invention claimed is:

1. A device adapted for use in a manufacturing process, the device comprising:

a chamber including a base and at least one sidewall extending upwardly from the base to form an apex, a longitudinal axis of the chamber extends from a center of the base to the apex, the chamber comprising an inlet, a first outlet, and a second outlet, wherein the chamber is configured to rotate around an axis of rotation in a direction perpendicular to the longitudinal axis of the chamber;

the first outlet residing generally in the center of the base;

the second outlet residing in the base and positioned adjacent to the first outlet;

the inlet residing in the base and positioned adjacent to the at least one sidewall, and the device further comprises a plurality of pumps and a plurality of valves coupled to the inlet and the first and second outlets, wherein, during rotation of the chamber, a first pump of the plurality of pumps is configured to continuously flow a complex starting material into the chamber through the inlet, a second pump of the plurality of pumps is configured to continuously flow separated solid slurry materials from the complex starting material out of the chamber through the first outlet and via a first valve of the plurality of valves, as supernatant materials from the complex starting material is pushed 3. The device of claim 1, wherein the chamber is a cone or a paraboloid.

4. The device of claim 1, wherein the device is comprised of a flexible or semi-flexible material surrounded by a rigid structure.

5. The device of claim 1, wherein the device is comprised of a rigid material.

6. The device of claim 1, wherein a desired product produced by the manufacturing process comprises solids, liquids, particles, or cells, and wherein all of surfaces of the device that come in contact with the desired product are disposable.

7. The device of claim 1, wherein a desired product is produced by a biotherapeutics process, a vaccine process, or a cell therapy manufacturing process and comprises solids, liquids, particles, or cells, and wherein all of surfaces of the device that come in contact with the desired product are reusable.

8. The device of claim 1, further comprising a programmable controller, a human machine interface, a motor, a plurality of valves, and a plurality of sensors, each of which are configured to control components of the device manually or automatically using preset process recipes.

9. The device of claim 1, further comprising a multichannel rotary union with seals configured to manage the flow of materials into and out of the chamber during rotation.

10. The device of claim 1, wherein the inlet flow rates can be automatically optimized using feedback from an optical sensor or a turbidity sensor.

11. A method using the device according to claim 1 according to one of the following groups (a)-(m):

(a) the device is used to separate materials based on difference in their sedimentation velocities;

(b) the device is used to isolate particles, cells, or solids from a mixture containing liquid;

(c) the device is used to isolate liquid from a mixture containing particles, cells, or solids;

(d) the device is used to wash particles or cells or to replace liquid in cell culture or slurry containing a different liquid and particles;

(e) the device is used as a cell retention system for a perfusion culture;

(f) the device is used to concentrate cells from one bioreactor and transfer the concentrated cells to another bioreactor;

(g) the device is used to separate cells from microcarriers;

(h) the device is used to transfect or infect cells;

(i) the device is used to coat particles with different materials;

(j) the device is used to separate different blood components;

(k) the device is used to purify materials using chromatography particles;

(l) the device is used to separate liquids based on their specific gravities; or (m) the device is used to separate solids or particles from a gas.

12. The device of claim 1, wherein the first outlet comprises a channel extending within the chamber from the base toward the apex of the chamber along the longitudinal axis and perpendicular to the axis of rotation of the chamber.

13. The device of claim 1, wherein separated materials having a higher density are configured to be continuously discharged through the first outlet and separated materials having a lower density are configured to be continuously discharged through the second outlet.

14. The device of claim 13, wherein the higher density separated materials comprise a solid slurry and the lower density separated materials comprise a clarified liquid.

15. The device of claim 1, wherein the chamber has a cross-sectional area that is constant for a distance from the base and then narrows to form the apex positioned on the longitudinal axis.

16. The device of claim 1, wherein the chamber has a cross-sectional area that narrows from the base to form the apex positioned on the longitudinal axis.

17. The device of claim 1, further comprising an umbilical tubing-based system that form continuous fluid paths to the inlet for flowing the complex starting material into the chamber and from the first or second outlets for flowing the separated materials out of the chamber during rotation.

18. The device of claim 1, wherein a partition resides in the chamber and extends from the base toward the apex of the chamber along the longitudinal axis and perpendicular to the axis of rotation.

19. The device of claim 1, wherein the inlet is positioned in the base of the chamber in a first position relative to the first outlet when the chamber is configured to rotate in a clockwise direction around the axis of rotation.

20. The device of claim 1, wherein a third pump of the plurality of pumps is configured to push fresh media into the chamber at a flow rate equal to the removal of the supernatant, thereby maintaining a constant volume within the chamber.

* * * * *